(12) United States Patent
Huang et al.

(10) Patent No.: US 10,877,235 B2
(45) Date of Patent: Dec. 29, 2020

(54) BALANCING DEVICE AND METHOD FOR BALANCING A MICROSCOPE

(71) Applicant: LEICA INSTRUMENTS (SINGAPORE) PTE. LTD., Singapore (SG)

(72) Inventors: Jason Huang, Singapore (SG); Chin Yi Liaw, Singapore (SG); Chee Bin Wong, Singapore (SG)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 30 days.

(21) Appl. No.: 16/257,236

(22) Filed: Jan. 25, 2019

(65) Prior Publication Data
US 2019/0235192 A1    Aug. 1, 2019

(30) Foreign Application Priority Data

Jan. 30, 2018 (EP) .................................... 18154229

(51) Int. Cl.
*G02B 7/00* (2006.01)
*G02B 21/00* (2006.01)
(Continued)

(52) U.S. Cl.
CPC .............. *G02B 7/001* (2013.01); *A61B 90/25* (2016.02); *A61B 90/50* (2016.02);
(Continued)

(58) Field of Classification Search
CPC .... G02B 7/001; G02B 21/0012; A61B 90/25; A61B 90/50; A61B 2090/5025;
(Continued)

(56) References Cited

U.S. PATENT DOCUMENTS 3,891,301 A * 6/1975 Heller ................ F16M 11/2035
359/384
5,480,114 A * 1/1996 Nakamura ........... F16M 11/126
248/123.2

(Continued)

*Primary Examiner* — Christopher Garft
(74) *Attorney, Agent, or Firm* — Hodgson Russ LLP

(57) ABSTRACT

The invention relates to a balancing device (14) for balancing a microscope (12) with respect to a rotation axis (1000), the balancing device (14) comprising a balancing weight (16) arranged around and assigned to the rotation axis (1000), such that the balancing weight (16) is rotatable around the rotation axis (1000), wherein a center of mass of the balancing weight (16) is arranged apart from the rotation axis (1000). The balancing device (14) further comprises a lever (18) for indicating a torque acting on the balancing device (14) and/or on the balancing weight (16), wherein the lever (18) is arranged around and assigned to the rotation axis (1000) to be rotatable around the rotation axis (1000), wherein the lever (18) extends within the balancing weight (16) and is movable by the torque within a predetermined range with respect to the balancing weight (16), and wherein an electrical potential of the lever (18) is set to a predetermined first potential value. Furthermore, the balancing device (14) comprises at least one stopper element (32), which is immobile with respect to the balancing weight (16) and forms at least one end point of the range of the lever (18), wherein the stopper element (32) and the lever (18) are in electrical contact when the lever (18) is arranged at the at least one end point of the range and wherein the lever (18) and the stopper element (32) are electrically isolated from each other when the lever (18) is apart from the at least one end point. In addition, the balancing device comprises control means configured to set an electrical potential of the stopper element (32) to a predetermined second potential value different from the first potential value at least when the lever (18) is apart from the at least one end point, to observe the electrical potential of the stopper element (32) and/or of (Continued)

Figure 1A:
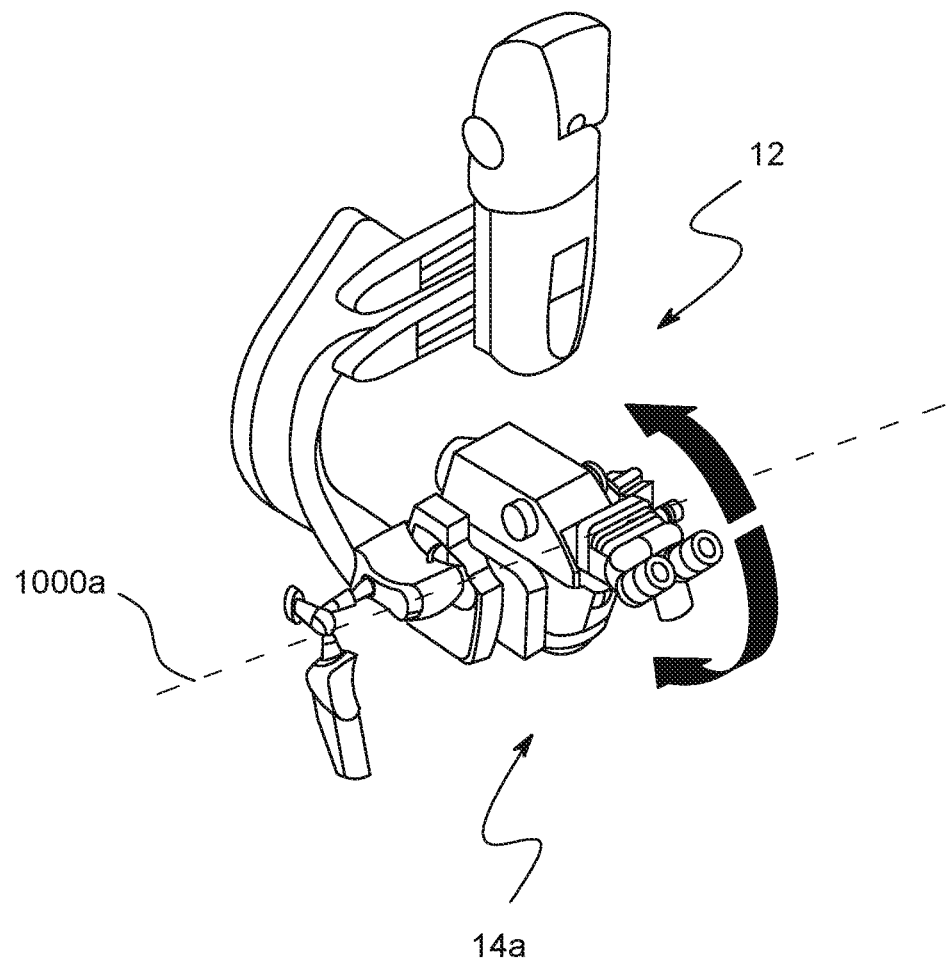

the lever (18) and to indicate the lever (18) being arranged at the first end point when the electrical potential of the stopper element (32) departs from the predetermined second potential value and/or when the electrical potential of the lever (18) departs from the predetermined first potential value. The invention further relates to a stand (10) for a microscope (12) and to a method for balancing a microscope (12).

16 Claims, 9 Drawing Sheets

(51) Int. Cl.
 *A61B 90/25* (2016.01)
 *A61B 90/50* (2016.01)
 *F16M 11/20* (2006.01)
(52) U.S. Cl.
 CPC ..... *F16M 11/2064* (2013.01); *G02B 21/0012* (2013.01); *A61B 2090/504* (2016.02); *F16M 2200/044* (2013.01)
(58) Field of Classification Search
 CPC ......... A61B 2090/506; F16M 11/2064; F16M 2200/044; F16M 11/2035; F16M 11/2042; F16M 11/2057; F16M 11/2071; F16M 2200/045
 See application file for complete search history.

(56) References Cited

U.S. PATENT DOCUMENTS

| | | | | |
|---|---|---|---|---|
| 5,651,718 A * | 7/1997 | Nakamura | ............. | A61B 90/25 248/123.2 |
| 5,667,186 A * | 9/1997 | Luber | .................... | F16M 11/08 248/550 |
| 5,812,301 A | 9/1998 | Nakamura | | |
| 6,045,104 A * | 4/2000 | Nakamura | ............. | F16M 11/10 248/123.11 |
| 6,050,530 A * | 4/2000 | Nakamura | ............. | A61B 50/28 248/123.2 |
| 6,129,319 A * | 10/2000 | Metelski | ................ | F16M 11/10 248/123.2 |
| 6,186,023 B1 * | 2/2001 | Nakamura | ........... | F16M 11/126 74/490.01 |
| 6,247,673 B1 * | 6/2001 | Bees | ..................... | F16M 11/10 248/123.11 |
| 2002/0074472 A1 * | 6/2002 | Gaida | .................... | G02B 7/001 248/276.1 |
| 2005/0247831 A1 * | 11/2005 | Nakamura | ............. | A61B 90/50 248/123.2 |
| 2014/0151522 A1 * | 6/2014 | Doi | .................... | F16M 11/2021 248/364 |
| 2014/0157937 A1 * | 6/2014 | Doi | .................... | F16M 11/2021 74/490.01 |

* cited by examiner

BALANCING DEVICE AND METHOD FOR BALANCING A MICROSCOPE

CROSS REFERENCE TO RELATED APPLICATIONS

This application claims priority of European patent application number 18154229.1 filed Jan. 30, 2018, the entire disclosure of which is incorporated by reference herein.

FIELD OF THE INVENTION

The present invention essentially relates to a balancing device and a method for balancing a microscope and, thus, is related to the field of stands for microscopes, in particular for surgical microscopes.

BACKGROUND OF THE INVENTION

Stands for microscopes are known in prior art, wherein the stands serve the purpose of supporting and balancing a microscope at a position with respect to the object to be observed, which is desired by the operator, e.g. a surgeon. The balancing plays a very crucial role when using the microscope, since it allows the microscope to maintain its position and/or orientation without the need for the operator to support or hold the microscope in the desired position. Typically, microscope stands comprise an A-balancing slide and a B-balancing slide, as well as a C-balancing device and a D-balancing device for balancing the microscope around several rotation axes. The balancing devices may be motorized and may be adapted to achieve an automated balancing of the microscope without requiring any interaction with the operator. When balanced, the microscope may also be locked in its position and/or orientation by means of brakes, which may be adapted as electromagnetic brakes, to prevent any unintentional movement of the microscope. For instance, the operator may be required to release the brakes in order to move the microscope to a different position and/or orientation.

For balancing the microscope with respect to a rotation axis, a precise determination of the position and/or orientation of the balancing device with regard to a balancing point, in which the balancing device will remain together with the attached components such as the microscope and possible other balancing devices, is necessary. In other words, it is necessary to precisely determine the position of the center of mass of the balancing device and the attached components with respect to the rotation axis, since the microscope will be balanced only with respect to the rotation axis, when its center of mass is located along the rotation axis.

Conventionally, a balancing device comprises a lever, which is movable in a predetermined range with respect to the balancing device around the rotation axis, wherein the predetermined range typically extends over only several tens of micrometers. When the balancing point is reached, i.e. when the microscope is balanced with regard to the rotational axis, no torque or only a negligible torque which is insufficient to overcome the counteracting friction forces of the balancing device, and, thus, no moving of the lever with respect to the other components of the balancing device, such as a balancing weight, will occur. Typically, when the lever is arranged in the middle of the range, in which the lever can be moved with respect to the balancing weight, the balancing point is reached. For precisely determining the position of the lever within its range of movement, at least one capacitive sensor is used, which is capable of outputting an electric signal in dependence of the lever's position. For instance, the capacitive sensors may output a voltage of +5 V when the lever is arranged on one side of the balancing point and output a voltage of 0 V when the lever is arranged on the other side of the balancing point, wherein the different positions with respect to the balancing points result in different distances of the lever from the capacitive sensor. By this, the balancing device can be automatedly adjusted to allow the balancing device reaching the balancing point and, thus, to balance the microscope. Usually, a stand for a microscope requires at least one capacitive sensor for each rotation axis, around which the microscope shall be balanced.

Therefore, this conventional technique and conventional balancing devices have the disadvantage that a large number of capacitive sensors are required. Since the capacitive sensors are very expensive and susceptible to damages, the capacitive sensors often have a significant influence on the costs for the manufacturing and maintenance of a balancing device and a stand for a microscope.

SUMMARY OF THE INVENTION

It is thus the objective technical problem of the invention to provide a method and a balancing device for balancing a microscope having a high or sufficient precision and requiring low costs in manufacturing and maintenance of the balancing device.

This problem is solved by a balancing device, a method for balancing a microscope and a stand for a microscope having the features of the respective independent claims. Preferred embodiments are subject-matters of the dependent claims.

In one aspect the invention relates to a balancing device for balancing a microscope with respect to a rotation axis. The balancing device comprises a balancing weight arranged around and fixed (i.e. assigned) to the rotation axis, such that the balancing weight is rotatable around the rotation axis, wherein a center of mass of the balancing weight is arranged apart from the rotation axis. The balancing device further comprises a lever for indicating a torque acting on the balancing device and/or on the balancing weight, wherein the lever is arranged around and fixed (i.e. assigned) to the rotation axis to be rotatable around the rotation axis, wherein the lever extends within the balancing weight and is movable by the torque within a predetermined range with respect to the balancing weight, and wherein an electrical potential of the lever is set to a predetermined first potential value. The balancing device also comprises at least one stopper element, which is immobile with respect to the balancing weight and forms at least one end point of the range of the lever, wherein the stopper element and the lever are in electrical contact when the lever is arranged at the at least one end point of the range and wherein the lever and the stopper element are electrically isolated from each other when the lever is apart from the at least one end point. Furthermore, the balancing device comprises control means such as an electrical control unit (i.e. a controller) configured to set an electrical potential of the stopper element to a predetermined second potential value different from the first potential value at least when the lever is apart from the at least one end point, to observe the electrical potential of the stopper element and/or of the lever and to indicate the lever being arranged at the first end point when the electrical potential of the stopper element departs from the predetermined second potential value and/or when the electrical potential of the lever departs from the predetermined first potential value.

In another aspect the invention relates to a stand for a microscope comprising at least one balancing device according to the invention for balancing the microscope.

In another aspect the invention relates to a method for balancing a microscope with respect to a rotation axis. The method comprises providing a balancing weight arranged around the rotation axis, such that the balancing weight is rotatable around the rotation axis, wherein a center of mass of the balancing weight is arranged apart from the rotation axis (step a). The method further comprises providing a lever for indicating a torque acting on the balancing device and/or on the balancing weight, wherein the lever is arranged around the rotation axis to be rotatable around the rotation axis, wherein the lever extends within the balancing weight and is movable by the torque within a predetermined range with respect to the balancing weight (step b) and setting an electrical potential of the lever to a predetermined first potential value (step c). In a step d) at least one stopper element is provided, which is immobile with respect to the balancing weight and forms at least one end point of the range of the lever, wherein the stopper element and the lever are in electrical contact when the lever is arranged at the at least one end point of the range and wherein the lever and the stopper element are electrically isolated from each other when the lever is apart from the at least one end point. An electrical potential of the stopper element is set to a predetermined second potential value different from the first potential value at least when the lever is apart from the at least one end point (step e). The method further comprises observing the electrical potential of the stopper element and/or the lever and indicating the lever being arranged at the first end point when the electrical potential of the stopper element departs from the predetermined second potential value and/or when the electrical potential of the lever departs from the predetermined first potential value (step f).

That the center of mass of the balancing device is arranged apart from the rotation axis may be necessary to balance a microscope, which may also have a center of mass being arranged apart from the rotation axis. The microscope may be balanced by arranging the balancing device and/or the balancing weight such that the common center of mass of the assembly of the microscope, the balancing device and eventual other components connected with the microscope and the balancing device is arranged along the rotation axis.

The lever may be essentially attached to the balancing weight, which means that the lever is movable with respect to the balancing weight only in a very small range, such that the range, in which the lever is movable only extends over few micrometers and/or millirad. The range may correspond to an angular range and/or a range for a translational movement. Preferably, the stopper element is arranged perpendicular or almost perpendicular to the lever, such that a movement of the lever results in a translational movement of the lever with respect to the stopper element, such that the lever increases or reduces the distance to the stopper element when carrying out a movement with respect to the balancing weight.

The stopper element may be adapted to mechanically block the movement of the lever with respect to the balancing weight at the first stopping point. In other words, the stopper element may serve as a latch or stop for the lever and thus form the first end point of the lever. The range of the lever may be restricted by one or more further end points, which may for instance be formed by a respective structure of the balancing weight.

The stopper element being in electrical contact with the lever means that electrical charges may be exchanged between the lever and the stopper element, when the electrical contact is established. The stopper element being electrically isolated from the lever means that no electrical charges may be exchanged directly and indirectly between the lever and the stopper element, when electrically isolated from each other.

That the control means are configured to set the electrical potential of the stopper element means that the control means may apply a voltage to the stopper element in order to add or withdraw electrical charges to or from the stopper element, respectively. That the control means are configured to observe the electrical potential of the stopper element means that the electrical potential of the stopper element can be determined, preferably measured by the control means. Preferably, setting and/or observing the electrical potential of the stopper element may be carried out continuously and/or in a repeated manner. Most preferably, setting and observing the electrical potential of the stopper element is carried out at different points in time, i.e. at a specific point in time the electrical potential is either set or observed. Most preferably, setting and observing the electrical potential, respectively, may be carried out in an alternating manner.

The invention provides the advantage that a balancing device can be provided at low manufacturing costs, because no expensive capacitive sensor is required. Therefore, the balancing device and/or a stand for a microscope comprising one or more such balancing devices can be provided at lower costs as compared to conventional stands comprising balancing devices using capacitive sensors.

In addition, the invention provides the advantage that the maintenance costs for the stand and/or for the balancing device may be reduced, because the one or more balancing devices are not equipped with a capacitive sensor, which my cause failures and/or may be required to be replaced or repaired.

Furthermore, the invention provides the advantage that a set up procedure and/or an alignment procedure of the balancing device and/or of a stand can be facilitated, since no "teaching" of the capacitive sensor is required. By this, the manufacturing costs and/or maintenance costs may be further reduced.

Preferably, the balancing device may be adapted as an A-balancing slide and/or as a B-balancing slide and/or as a C-balancing device and/or as a D-balancing device for a stand for a microscope. In other words, the balancing device may be used for balancing a microscope with respect to any rotation axis, around which the microscope needs to be balanced. Thus, most preferably the stand comprises several balancing devices for balancing the microscope with respect to several different rotation axes.

Preferably, the control means comprise a control unit, which is electrically connected to the stopper element to set and observe the electrical potential of the stopper unit. The control unit may comprise further functionalities related to the balancing of the microscope or related to other tasks.

Preferably, one of the first potential value and the second potential value is equal to the ground potential and wherein the other one of the first potential and the second potential deviates from the ground potential by at least 1 V, preferably at least 2 V, more preferably 3 V, much more preferably at least 4 V, most preferably at least 5 V, and wherein the other one of the first potential and the second potential deviates from the ground potential not more than 20 V, preferably not more than 15 V, most preferably not more than 10 V. In other words, one of the lever and the stopper element may be grounded, wherein the other one of the lever and the stopper element is kept at a higher or lower electrical potential than the ground potential. This allows a reliable detection of the change in electrical potential of the stopper element, when the stopper element comes into electrical contact with the lever.

Optionally the stopper element may be configured as a stopper screw, wherein the stopper screw is adjustable to change the position of the first end point of the range of the lever. This allows a precise adjustment of the range in which the lever may move with respect to the balancing weight. Preferably the range of the lever determines a maximum distance the lever may move from the first end point to a second end point, which extends over at least 5 µm, preferably at least 10 µm, more preferably at least 20 µm, most preferably at least 30 µm and/or extends over not more than 100 µm, preferably not more than 75 µm, more preferably not more than 50 µm, most preferably not more than 40 µm.

Preferably the at least one stopper element is a first stopper element forming a first end point of the range of the lever and the balancing device further comprises at least a second stopper element, which is immobile with respect to the balancing weight and forms a second end point of the range of the lever, wherein the second stopper element and the lever are in electrical contact when the lever is arranged at the second end point of the range and wherein the lever and second the stopper element are electrically isolated from each other when the lever is apart from the second end point. More preferably the control means are further configured to set an electrical potential of the second stopper element to a predetermined third potential value different from the first potential value at least when the lever is apart from the second end point, to observe the electrical potential of the second stopper element and to indicate the lever being arranged at the second end point when the electrical potential of the second stopper element departs from the predetermined third potential value. Most preferably the third potential is equal to the second potential. This allows determining the position of the lever not only at the first end point but also at the second end point of the range in which the lever can be moved. This may allow faster and/or facilitated and/or more efficient balancing of the balancing device as compared to other embodiments, according to which only the position at one (the first) end point is determined.

Preferably, the stopper element is electrically isolated with respect to the balancing weight. This allows a reliable electrical separation of the stopper element and the lever to ensure that the electrical potential of the stopper element, which indicates the stopper reaching the first end point, only occurs when the lever indeed does mechanically and electrically contact the stopper element.

Preferably the balancing device is motorized and/or adapted to automatedly balance a microscope with respect to a rotation axis. This allows an automated adjustment of the balancing weights, i.e. an automated balancing, which is carried out optionally by means of the control unit.

Preferably the method for balancing the microscope further comprises the steps of rotating the balancing weight and the lever around the rotation axis such that the lever is in electrical contact with the stopper element, if the lever is not yet in electrical contact with the stopper element (step g) and rotating the balancing weight and the lever in the opposite direction as in step g) with a predetermined amplitude such that the lever is arranged at a predetermined position within the predetermined range (step h). This allows a reliable and efficient automated balancing of the balancing weight and/or the microscope without requiring a capacitive sensor.

Further advantages and embodiments of the invention will become apparent from the description and the appended figures.

It should be noted that the previously mentioned features and the features to be further described in the following are usable not only in the respectively indicated combination, but also in further combinations or taken alone, without departing from the scope of the present invention.

In the following, preferred embodiments of the invention will be detailed with reference to the appended figures without limiting the invention to these preferred embodiments.

BRIEF DESCRIPTION OF THE DRAWING VIEWS

In the drawings:

FIGS. 1A to 1D illustrate an exemplary stand supporting a microscope according to a preferred embodiment.

Figure 2:
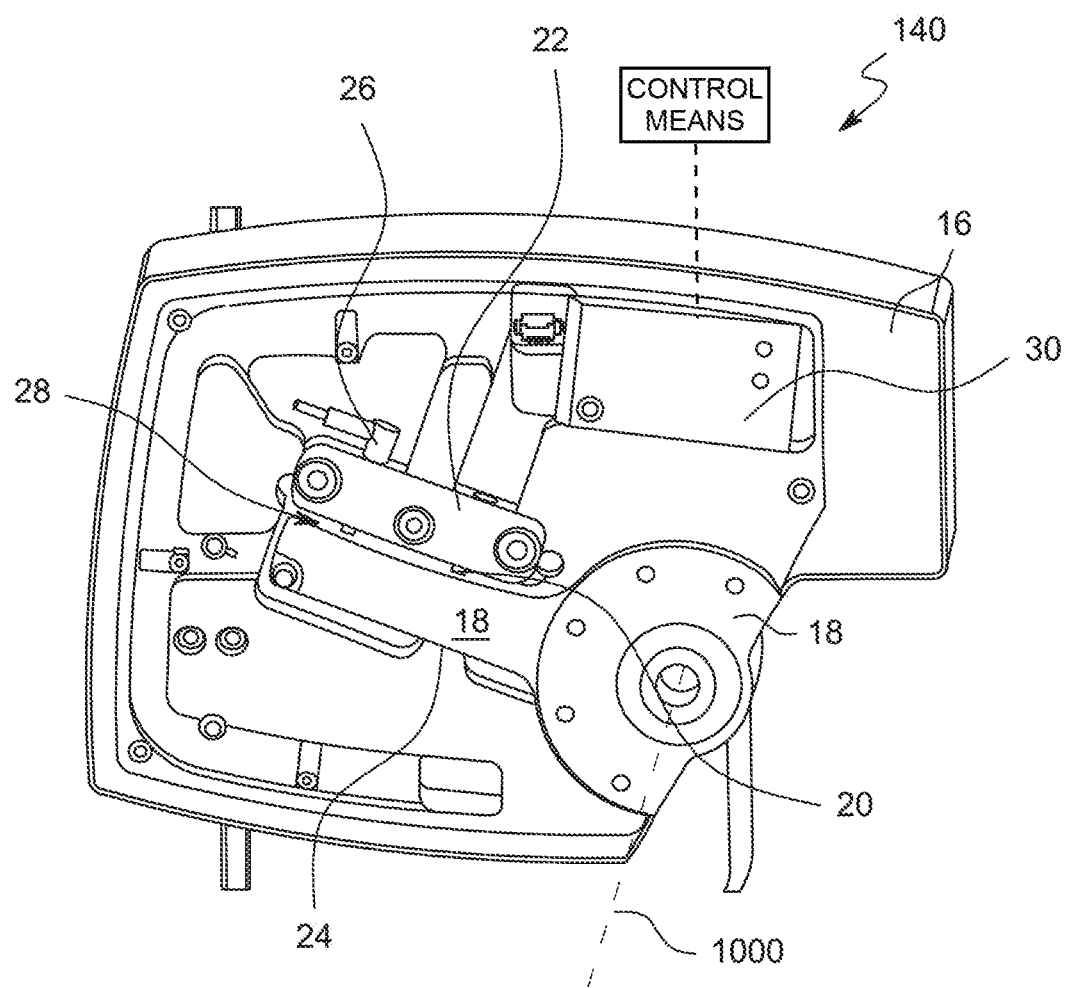

FIG. 2 schematically shows a conventional balancing device known in prior art in a perspective illustration.

Figure 3A:
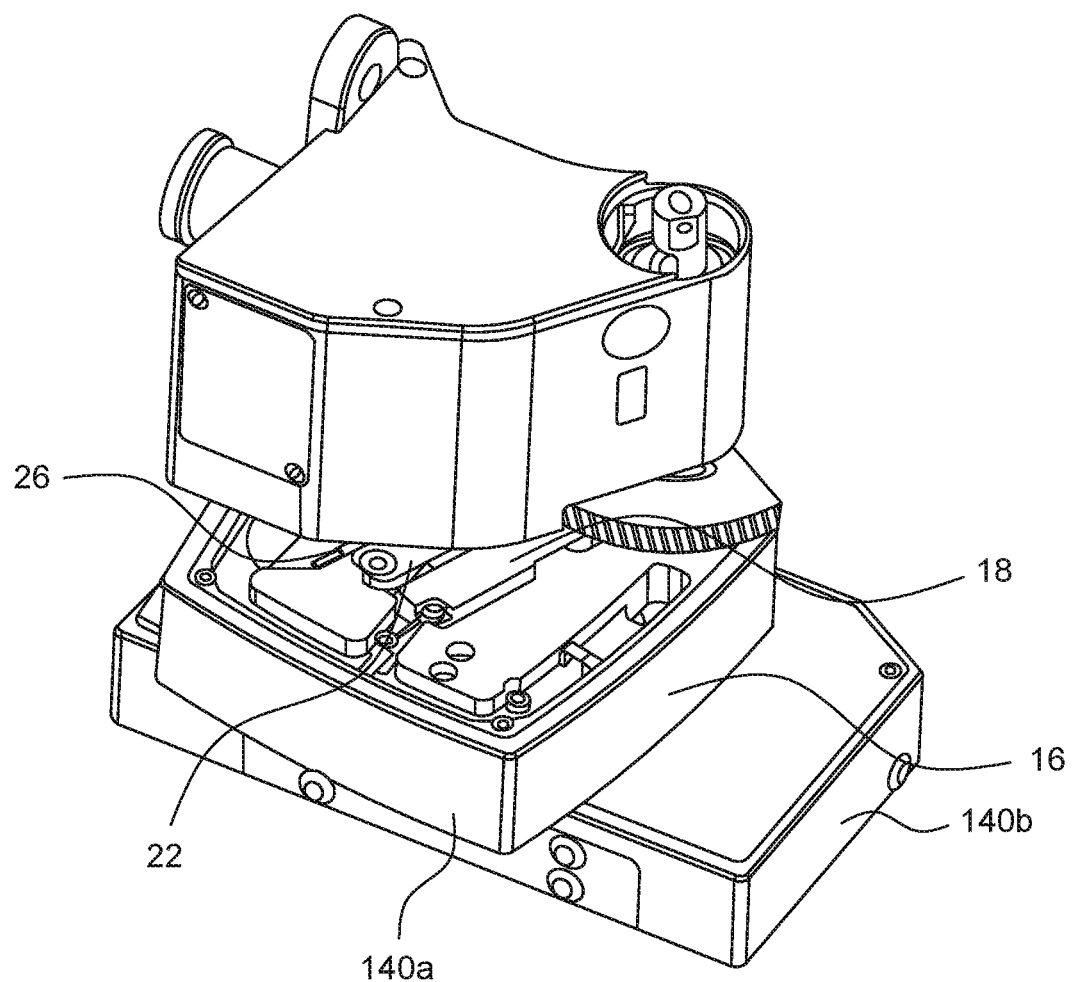
Figure 3B:
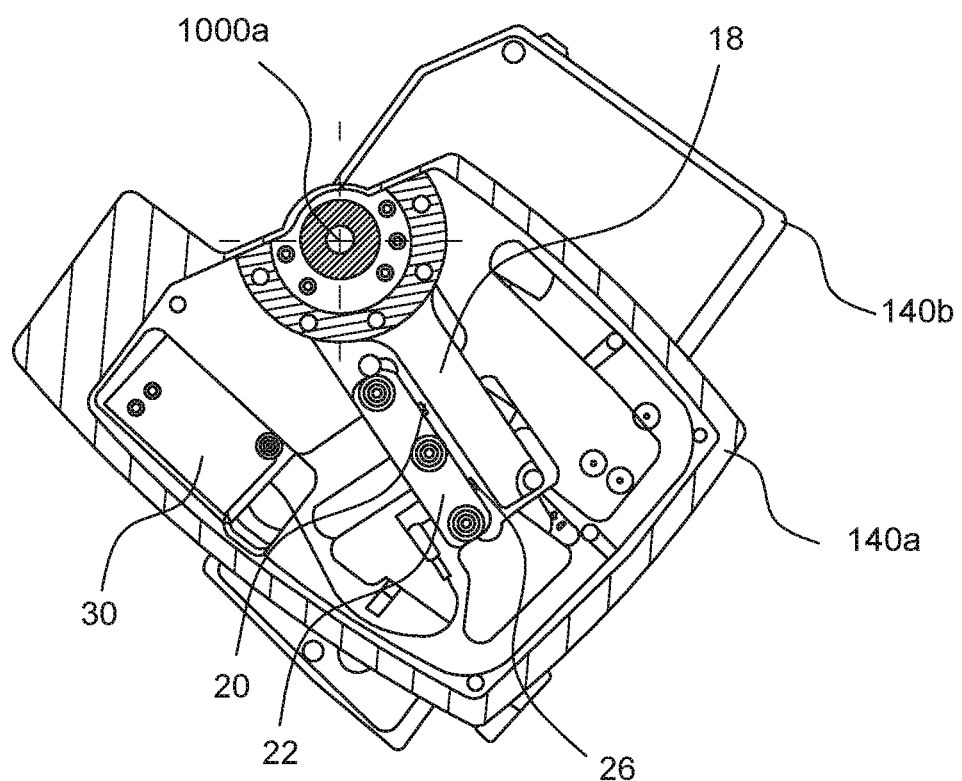

FIGS. 3A and 3B show the conventional balancing device of FIG. 2 in a perspective view (FIG. 3A) and in a sectional view (FIG. 3B).

Figure 4A:
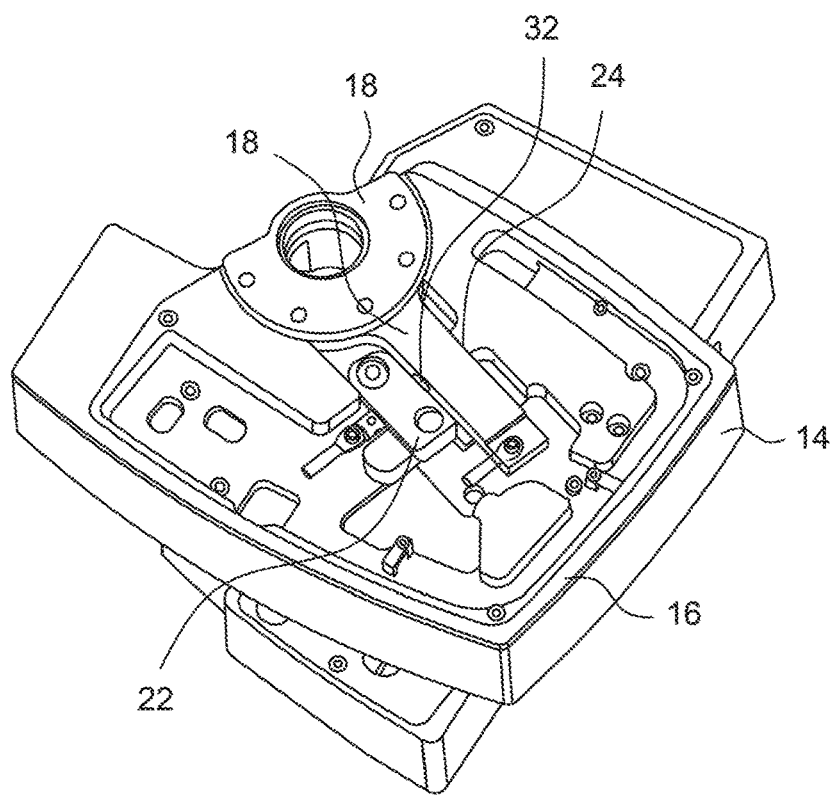
Figure 4B:
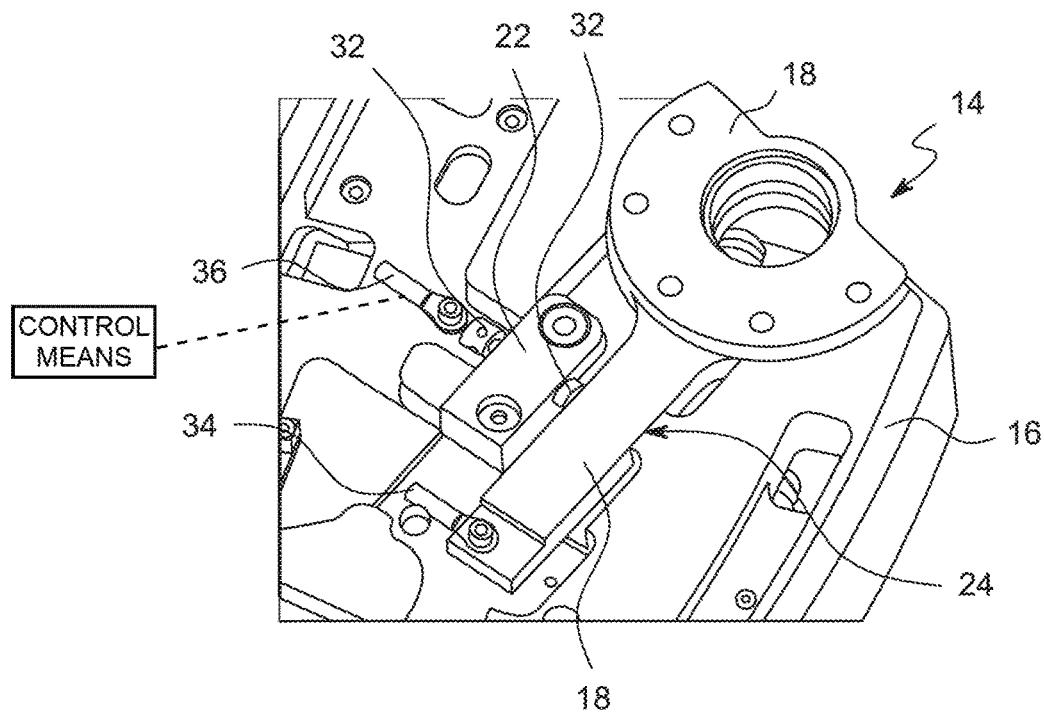

FIGS. 4A and 4B schematically depict a balancing device according to a preferred embodiment of the invention.

Figure 5:
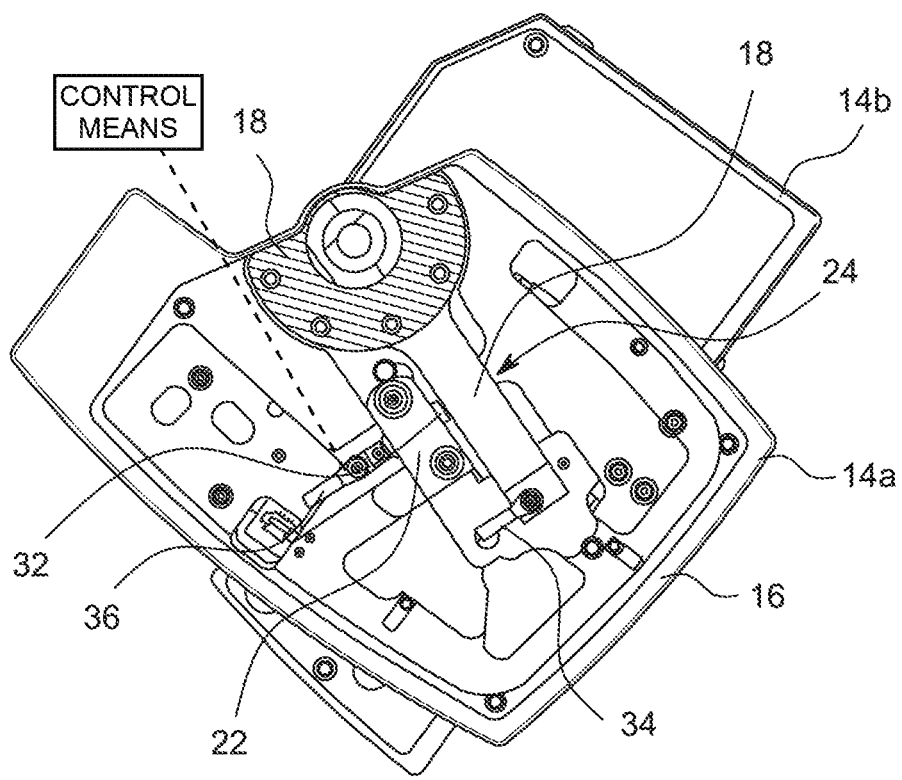

FIG. 5 shows the balancing device according to the preferred embodiment discussed with reference to FIGS. 4A and 4B in a schematic sectional view.

DETAILED DESCRIPTION OF THE INVENTION

Figure 1B:
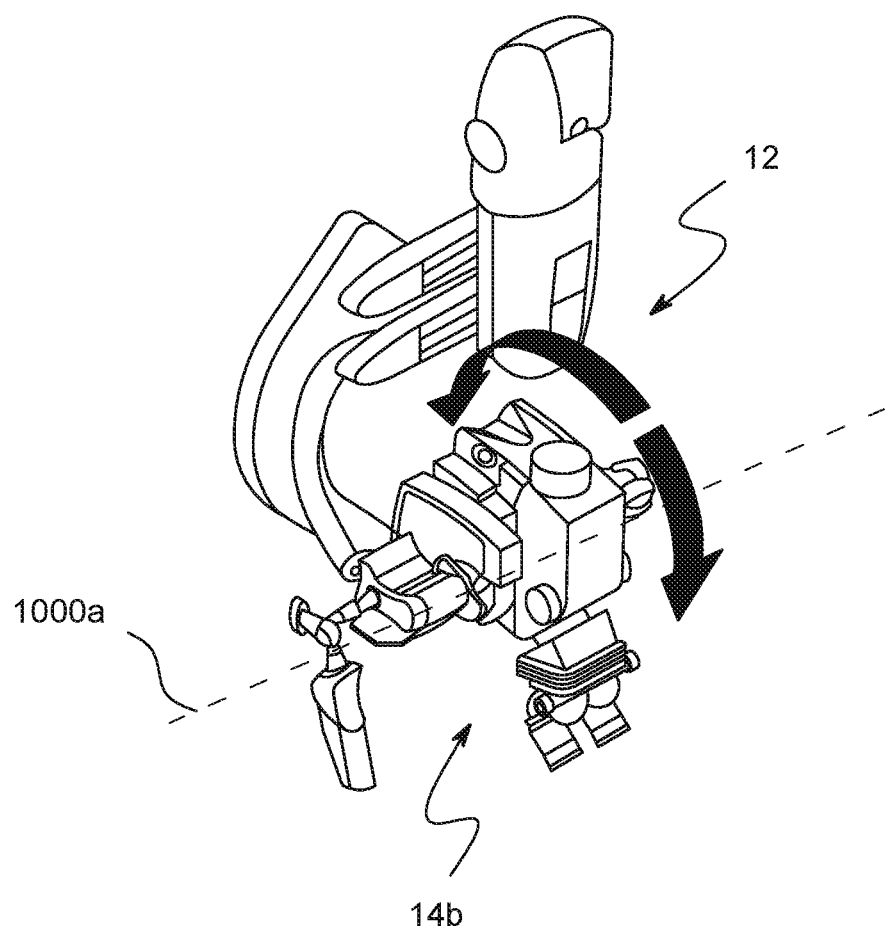
Figure 1C:
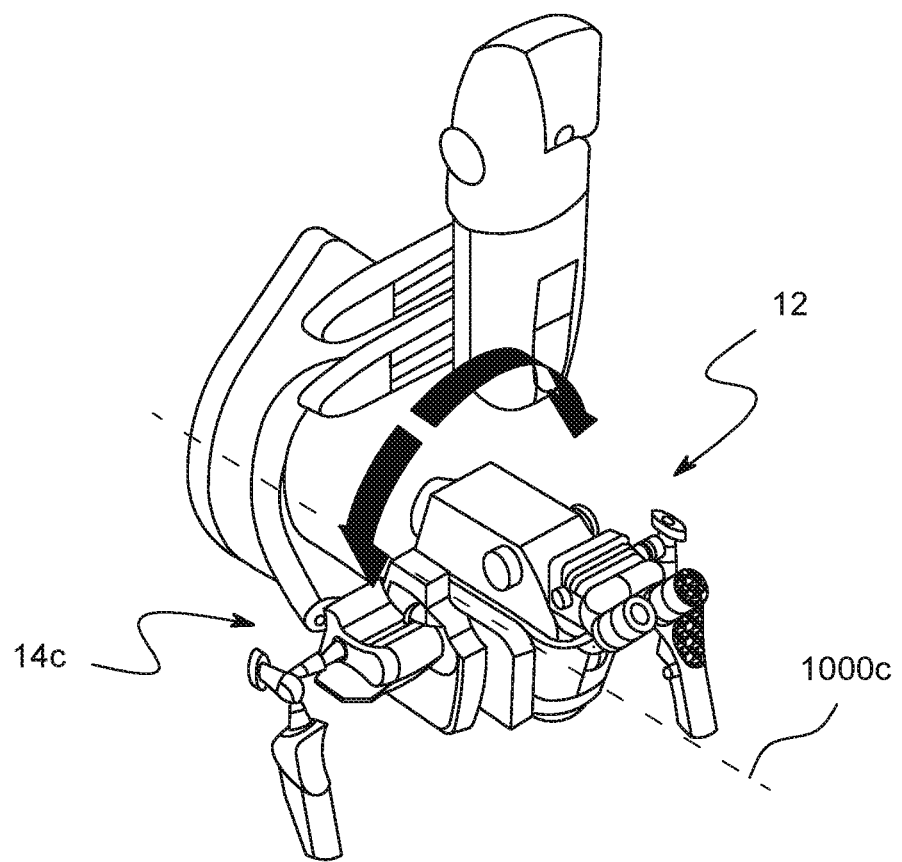
Figure 1D:
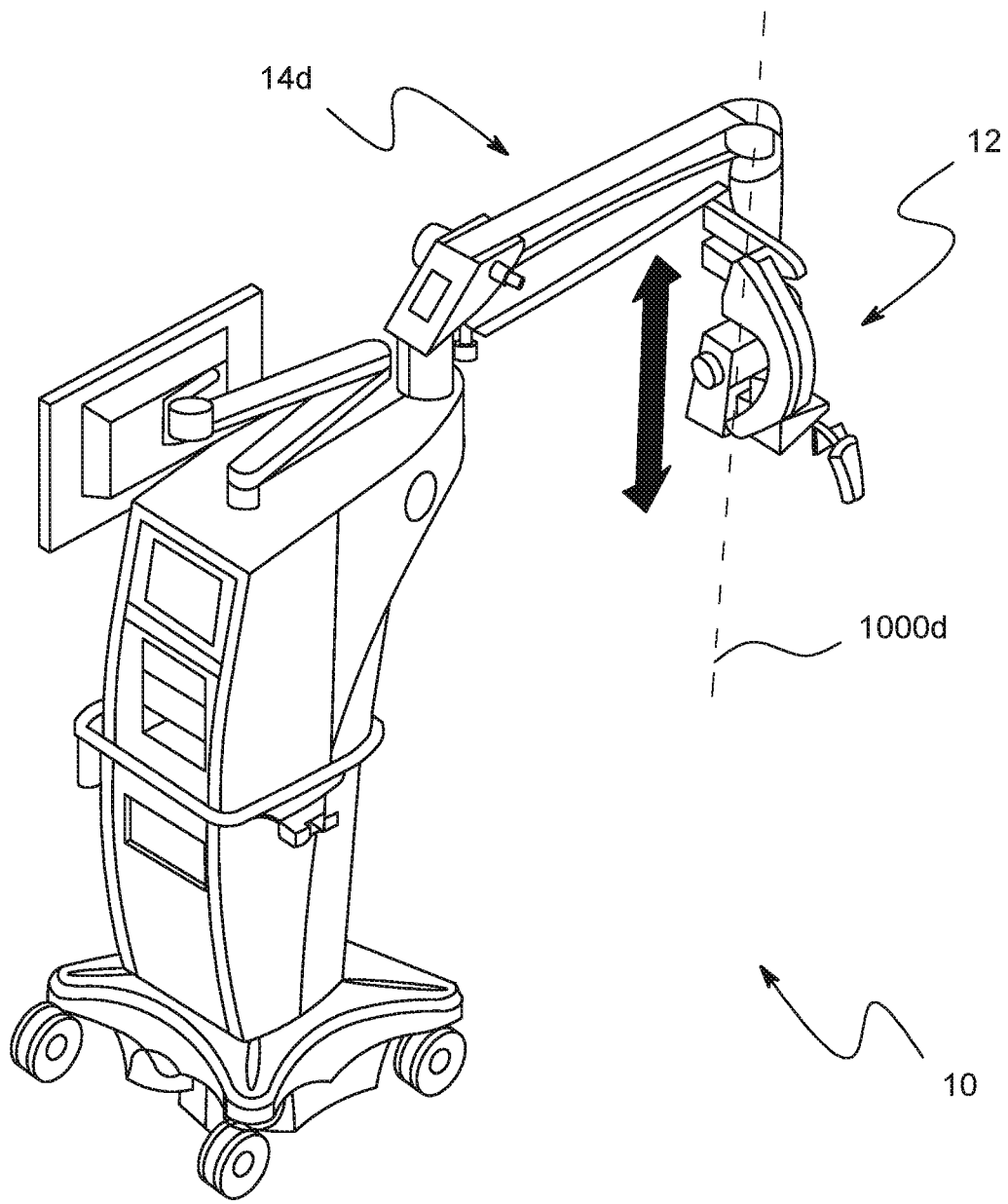

FIGS. 1A to 1D illustrate an exemplary stand 10 supporting a microscope 12, wherein the stand 10 comprises several balancing devices 14, each for balancing the microscope 12 with respect to a specific rotation axis. FIG. 1A indicates a balancing device 14a for balancing the microscope with respect to the rotation axis 1000a, wherein the balancing device 14a is configured as an A-balancing slide. FIG. 1B shows a balancing device 14b configured as a B-balancing slide, which is also adapted to balance the microscope 12 around the rotation axis 1000a in a different orientation. The balancing devices 14a and 14b, i.e. the A-balancing slide and the B-balancing slide, may form together an AB-balancing unit. FIG. 1C illustrates a balancing device 14c for balancing the microscope 12 around a rotation axis 1000c, wherein the balancing device 14c may be adapted as a C-balancing device. FIG. 1D depicts a whole stand 10 and in particular a balancing device 14d for balancing the microscope 12 and the stand 10 along a D-axis 1000d, wherein the balancing device 14d is adapted as a D-balancing device.

FIG. 2 schematically shows a conventional balancing device 140 known in prior art in a perspective illustration. This balancing device comprises a balancing weight 16, which may be formed from massive or bulk metal and which houses other components of the balancing device. The balancing device 140 further comprises a lever 18, which is adapted to be mounted to a shaft (not shown) extending along the rotation axis 1000 around which the balancing device 140 is adapted to balance a microscope 12 by means of the balancing weight 16. The lever 18 is attached to the shaft and/or to the balancing weight 16 such as to be movable in a small range, particular in a small angular range, with respect to the balancing weight 16. On one side, the range in which the lever 18 can be moved is limited by the blocking element 20, which may mechanically hinder a further movement of the lever 18 in the direction towards the blocking element 20. The blocking element 20 is mechanically fixed to the balancing weight 16 and may be adjustable such as to allow an adjustment of the range, in which the lever 18 is movable, and thus the blocking element 20 forms a first end point of the range of the lever 18. The other end point is formed by a respective blocking structure 24 of the balancing weight 16 itself, which hinders a further movement of the lever 18 in the other direction. The blocking element 20 is held by a support element 22, which may be separately attached to the balancing weight 16. The support element 22 further supports a capacitive sensor 26, which is attached in a through-hole in the support element, such that a sensing surface 28 of the capacitive sensor 26 faces the lever 18 and allowing the capacitive sensor 26 to output an electric signal depending on the distance of the lever 18 from the sensing surface 28. The balancing weight 16 further houses a sensor board 30, which is in communication with the capacitive sensor 26 and may comprise a computational unit for evaluating the signals provided by the capacitive sensor 26 and eventually providing information regarding the balancing to a control unit (not shown) of the stand. The blocking element 20 is attached to the balancing weight 16 such as to provide a gap of only about 30 to 40 μm, in which the lever can be moved with respect to the balancing weight. The capacitive sensor 26 is attached to the balancing weight 16 such as to be about 200 μm spaced from the lever 18, when the lever 18 is located at the first end point defined by the stopper element 20, i.e. when the lever 18 is closest to the capacitive sensor 26.

FIGS. 3A and 3B show the conventional balancing device 140 of FIG. 2 in a perspective view (FIG. 3A) and in a sectional view (FIG. 3B). The balancing device 140 is adapted as an A-balancing slide and may contribute to balancing a microscope 12 around an A-balancing rotation axis 1000*a*. The balancing device 140 may be attached to a B-balancing slide 140*b*.

FIGS. 4A and 4B schematically depict a balancing device 14 according to a preferred embodiment of the invention. In some aspects and features this balancing device 14 resembles the previously discussed conventional balancing device 140. For this reasons, the components, which are also present in the conventional balancing device 140, are indicated with the same reference signs. However, the balancing device 14 according to this preferred embodiment of the invention differs from the conventional balancing device 140 in particular by the fact that it does not comprise a capacitive sensor. The support element 22 supports a stopper element 32, which is adapted as a stopper screw and extends through a through-hole in the support element 22. The stopper element 32 is fixed by the support element 22 such as to form a first end point of the range, in which the lever 18 can be moved. The stopper element 32 is at least partially electrically conductive and has in particular an electrically conductive surface facing the lever 18. The lever 18 is electrically grounded by means of a contacting element 34, which is attached to the surface of the (conductive) lever 18 and which may be connected to a conductive element having ground potential. The stopper element 32 is connected by a further connection element 36, by means of which the stopper element 32 is brought to an electrical potential being higher or lower than the ground potential, preferably +5V (with respect to the ground potential), to establish a voltage between the lever 18 and the stopper element as long as the lever 18 is not in contact with the stopper element 32. The balancing device is particularly adapted such that the stopper element 32 is electrically isolated from the lever and optionally from other components having ground potential, as for instance the balancing weight 16, as long as the lever 18 is not in contact with the stopper element 32. For example, the support element 22 may be formed at least partly from electrically isolating material to ensure good electrical isolation of the stopper element 32 from the ground potential. This allows reliably setting the electrical potential of the stopper element 32 to the desired voltage deviating from the ground potential. For instance, the stopper element 32 may be connected via the contacting element 36 to a control unit, which may set the electrical potential of the stopper element 32 to the desired first potential value, for instance +5 V, and to observe the electrical potential of the stopper element 32.

When the lever 18 is arranged in the first end point and by doing so touches the stopper screw 32 an electrical contact between the lever 18 being at the second potential value, i.e. being at ground potential, with the stopper element 32 being at the first potential value, electrical charges will flow between the lever 18 and the stopper element 32 and the electrical potential of the stopper element 32 will change. This change in electrical potential can be observed, i.e. for example measured, by the control unit connected via the connection element 36 to the stopper element 32 and, hence, the control unit can detect that the lever 18 is in mechanical (and electrical) contact with the stopper element 32. Consequently, the control unit detects that the lever 18 is arranged at the first end point. Therefore, the balancing procedure can be started to move the balancing device 14 starting from the position, in which the lever 18 is at the first end point, such that the lever 18 moves away from the first end point and reaches a desired balancing point, which is preferably located in the middle of the range, in which the lever 18 can be moved. The movement, which is necessary to balance the balancing device and the microscope, depends on the system and the specific weights and inertial moments of the microscope and the balancing devices, and thus, the required movements can be predetermined by the manufacturer of the stand 10 and/or the microscope 12. The required movement may for instance comprise a push of the balancing device 14 in a direction around the respective rotation axis 1000 such that the balancing point may be reached and the lever 18 reaches the predetermined balancing point in the gap between the two end points of its range of movement.

The predetermined movement, which is required for the balancing device 14 to reach the balancing point may be require an orientation of the balancing device 14, in which the lever 18 is essentially in contact with the stopper element 32 without additional torque, which would press the lever 18 against the stopper element 32. In case, however, the lever 18 is pressed by a certain torque against the stopper element 32, the balancing procedure may include stepwise movements, preferably using very small steps, of the balancing device 14 in a direction to reduce this torque, until reaching the point at which the lever 18 releases the contact with the stopper element 32. At this very specific point, the balancing device 14 again is arranged such that there is no torque between the lever 18 and the stopper element 32. By choosing the step size sufficiently small, the deviation from the point, at which the lever 18 is in contact with the stopper element 32 but is not pressed towards the stopper element 32, may be realized sufficiently small for achieving a sufficient precision for adequate balancing.

FIG. 5 shows the balancing device 14a according to another preferred embodiment in a schematic sectional view, wherein the balancing device is configured as an A-balancing device 14a and is connected with a further B-balancing device 14b. According to this preferred embodiment also the electrical potential of the blocking structure 24 is determined and/or controlled and/or set by the control unit. The blocking structure 24, in particular the surface of the blocking structure 24, which may be contacted by the lever 18 when reaching the second end point, is electrically isolated from the balancing weight and its electrical potential may be kept by the control unit at a third potential value differing from the first potential value, i.e. differing from the electrical potential value of the lever 18 when not in contact with the lever. The third potential value may be equal to or different from the second potential value of the stopper screw 32 at the first end point. The blocking structure 24 forming the second end point may also be referred to as a further or second stopper element and/or may also be configured as a stopper screw.

When the lever 18, which is kept at the first potential value, which may be ground potential, comes into electrical contact with the blocking structure 24, the electrical potential of the blocking structure 24 will change at least for a short period of time, by which the position of the lever 18 can be determined as the second end point.

The method for balancing the balancing device based on this preferred embodiment may comprise determining whether the lever is either arranged at the first end point or at the second end point by determining the electrical potential of the stopper screw 32 and/or of the blocking structure 24 and/or of the lever 18. If the lever 18 is determined not to be at the first or second end point, the balancing device is moved around the rotational axis until the lever 18 reaches the first or the second end point. Afterwards, the balancing device 14 is moved into the opposite direction until the other end point is reached, wherein the required time for moving the lever from one to the other end point is measured. Then the balancing device is stopped, for instance by stopping the motor.

Finally, for reaching the balancing point the balancing device 14 is moved again in a reversed direction (to the now opposite end point) with the same power and/or velocity but only for a time duration, which equals to about half of the previously measured time duration that was required for traveling the lever 18 from one to the opposite end point. By this, the balancing point, which may be in the middle of the range, in which the lever 18 can be moved, may be reached. The time duration, for which the balancing device 14 is moved to reach the balancing point, may be varied and/or modified and/or manipulated for optimizing the balancing point for different balancing devices and/or systems which may have different moments of inertia.

LIST OF REFERENCE SIGNS 10 stand (for a microscope)
12 microscope
14, 14a, 14b, 14c, 14d balancing device
140 (conventional) balancing device
16 balancing weight
18 lever
20 blocking element
22 support element
24 blocking structure
26 capacitive sensor
28 sensing surface
30 sensor board
32 stopper element
34 contacting element (for the lever)
36 contacting element (for the stopper element)
1000, 1000a, 1000c, 1000d rotation axis

What is claimed is:

1. A balancing device (14) for balancing a microscope (12) with respect to a rotation axis (1000), the balancing device (14) comprising:
   a balancing weight (16) arranged around the rotation axis (1000) such that the balancing weight (16) is rotatable around the rotation axis (1000), wherein a center of mass of the balancing weight (16) is arranged apart from the rotation axis (1000);
   a lever (18) for indicating a torque acting on the balancing device (14) and/or on the balancing weight (16), wherein the lever (18) is arranged around the rotation axis (1000) to be rotatable around the rotation axis (1000), wherein the lever (18) extends within the balancing weight (16) and is movable by the torque within a predetermined range with respect to the balancing weight (16), and wherein an electrical potential of the lever (18) is set to a predetermined first potential value;
   at least one stopper element (32), which is immobile with respect to the balancing weight (16) and forms at least one end point of the range of the lever (18), wherein the stopper element (32) and the lever (18) are in electrical contact when the lever (18) is arranged at the at least one end point of the range and wherein the lever (18) and the stopper element (32) are electrically isolated from each other when the lever (18) is apart from the at least one end point;
   a control means connected to the stopper element, wherein the control means is configured to set an electrical potential of the stopper element (32) to a predetermined second potential value different from the first potential value at least when the lever (18) is apart from the at least one end point, to observe the electrical potential of the stopper element (32) and/or the electrical potential of the lever (18), and to indicate the lever (18) being arranged at one of the least one end points when the electrical potential of the stopper element (32) departs from the predetermined second potential value and/or when the electrical potential of the lever (18) departs from the predetermined first potential value.

2. The balancing device (14) according to claim 1, wherein the balancing device (14) is adapted as at least one of an A-balancing slide (14a), a B-balancing slide (14b), a C-balancing device (14c), and a D-balancing device (14d) for a stand for a microscope (12).

3. The balancing device (14) according to claim 1, wherein the control means comprises a control unit electrically connected to the stopper element (32) to set and observe the electrical potential of the stopper element (32).

4. The balancing device (14) according to claim 1, wherein one of the first potential value and the second potential value is equal to the ground potential and wherein the other one of the first potential and the second potential deviates from the ground potential by at least 1 V and by not more than 20V.

5. The balancing device (14) according to claim 4, wherein one of the first potential value and the second potential value is equal to the ground potential and wherein the other one of the first potential and the second potential deviates from the ground potential by at least 5 V and by not more than 10V.

6. The balancing device (14) according to claim 1, wherein the stopper element (32) is a stopper screw, wherein the stopper screw is adjustable to change the position of one of the at least one end points of the range of the lever (18).

7. The balancing device (14) according to claim 1, wherein the stopper element (32) is electrically isolated with respect to the balancing weight (16).

8. The balancing device (14) according to claim 1, wherein the balancing device (14) is motorized and/or adapted to automatedly balance a microscope (12) with respect to a rotation axis (1000).

9. The balancing device (14) according to claim 1, wherein the at least one stopper element (32) is a first stopper element (32), and wherein the balancing device (14) further comprises a second stopper element (24) which is immobile with respect to the balancing weight (16) and forms a second end point of the range of the lever (18), wherein the second stopper element (24) and the lever (18) are in electrical contact when the lever (18) is arranged at the second end point of the range and wherein the lever (18) and second the stopper element (24) are electrically isolated from each other when the lever (18) is apart from the second end point; and
wherein the control means is further configured to set an electrical potential of the second stopper element (24) to a predetermined third potential value different from the first potential value at least when the lever (18) is apart from the second end point, to observe the electrical potential of the second stopper element (24), and to indicate the lever (18) being arranged at the second end point when the electrical potential of the second stopper element (24) departs from the predetermined third potential value.

10. The balancing device (14) according to claim 9, wherein the third potential value is equal to the second potential value.

11. The balancing device (14) according to claim 1, wherein the range of the lever (18) corresponds to a maximum distance the lever travels from a first end point to a second end point, wherein the range extends at least 5 μm and not more than 100 μm.

12. The balancing device (14) according to claim 11, wherein the range of the lever (18) extends at least 30 μm and not more than 40 μm.

13. A stand for a microscope (12) comprising at least one balancing device (14) according to claim 1 for balancing the microscope (12).

14. The stand (10) for a microscope (12) according to claim 13, comprising several balancing devices (14) according to claim 1 for balancing the microscope (12) with respect to several different rotation axes (1000).

15. A method for balancing a microscope (12) with respect to a rotation axis (1000), the method comprising the steps:
a) providing a balancing device (14) as set forth in claim 1 for balancing the microscope (12) with respect to the rotation axis (1000);
b) setting the electrical potential of the lever (18) of the balancing device (14) to the predetermined first potential value;
c) setting the electrical potential of the at least one stopper element (32) of the balancing device (14) to the predetermined second potential value different from the first potential value at least when the lever (18) is apart from the at least one end point; and
d) observing the electrical potential of the stopper element (32) and/or the lever (18) and indicating the lever (18) being arranged at the at least one end point when the electrical potential of the stopper element departs from the predetermined second potential value and/or when the electrical potential of the lever (18) departs from the predetermined first potential value.

16. The method according to claim 15, wherein the method further comprises the following steps:
e) rotating the balancing weight (16) of the balancing device (14) and the lever (18) around the rotation axis (1000) in a first direction such that the lever (18) is in electrical contact with the stopper element (32), if the lever (18) is not yet in electrical contact with the stopper element (32); and
f) rotating the balancing weight (16) and the lever (18) in a second direction opposite the first direction of step (g) with a predetermined amplitude such that the lever (18) is arranged at a predetermined position within the predetermined range.

* * * * *